United States Patent [19]

Reed

[11] Patent Number: 4,905,505

[45] Date of Patent: Mar. 6, 1990

[54] METHOD AND SYSTEM FOR DETERMINING VAPOR PRESSURE OF LIQUID COMPOSITIONS

[75] Inventor: Donald B. Reed, Plano, Tex.

[73] Assignee: Atlantic Richfield Company, Los Angeles, Calif.

[21] Appl. No.: 318,381

[22] Filed: Mar. 3, 1989

[51] Int. Cl.[4] .............................................. G01N 7/00
[52] U.S. Cl. .......................................... 73/64.2; 73/53
[58] Field of Search .................. 73/61 R, 53, 19, 64.2

[56] References Cited

U.S. PATENT DOCUMENTS 4,301,676 11/1981 Gokcen ................................. 73/64.2
4,733,557 3/1988 Baillie et al. .......................... 73/64.2

Primary Examiner—Hezron E. Williams
Attorney, Agent, or Firm—Michael E. Martin

[57] ABSTRACT

The vapor pressure of a multi-component liquid composition is measured by providing an eductor through which the liquid composition is caused to flow at selected inlet pressures to provide incrementally changing pressure differentials across the eductor. The pressure differential is read for each incremental change across the eductor and the suction port pressure is read at each incremental pressure differential until the suction port pressure as a function of the pressure differential indicates a change in slope or point of inflection along the so-called dead fluid curve indicating the bubble point or true vapor pressure of the liquid composition. A motorized pressure regulator valve may be interposed in the liquid composition flow conduit upstream of the eductor for incrementally changing the pressure differential. The point of inflection may be obtained by determining the mathematical relationship using the cubic spline fit technique and calculating the second derivative of the function of the suction port pressure versus the pressure differential across the eductor until the second derivative equals zero.

8 Claims, 2 Drawing Sheets

METHOD AND SYSTEM FOR DETERMINING VAPOR PRESSURE OF LIQUID COMPOSITIONS

BACKGROUND OF THE INVENTION

1. Field of the Invention

The present invention pertains to a method for determining the vapor pressure of a multi-component liquid, such as crude oil, using an eductor and associated equipment for determining the change in the slope of a curve which represents the change in the suction port pressure of the eductor as a function of the pressure differential across the eductor.

2. Background

Measurement of the vapor pressure of a multi-component liquid is difficult in that the various compositions of the liquid typically have different vapor pressures at a particular temperature. Conventional vapor pressure measurement techniques and systems perform operations to reduce the pressure acting on a sample of liquid in a controlled environment until the pressure remains substantially constant, indicating that the vapor pressure of the liquid has been reached. However, as certain components of a multi-component fluid vaporize, the vapor pressure of the remaining liquid changes to a different value. This phenomenon complicates conventional vapor pressure measurement techniques and results in inaccurate determinations of the true vapor pressure of a particular liquid composition.

The aforementioned deficiencies in conventional vapor pressure measurement techniques may be of particular concern when attempting to measure the vapor pressure of liquids such as crude petroleum which have various hydrocarbon compositions mixed therein. The handling and transport of such a liquid should usually be controlled to prevent unwanted vaporization of the lower molecular weight liquids during the transport and storage processes.

One relatively uncomplicated device for measuring vapor pressure of a liquid utilizes an eductor. Conventional eductor-type vapor pressure measurement devices operate to provide a liquid flow rate through the eductor such that a relatively large pressure drop across the eductor is assured whereby measurement of the flow stream pressure at the so-called suction port of the eductor provides for measurement of a vapor pressure condition of at least one component of a multi-component liquid. However, use of an eductor type system may not be accurate if the liquid to be measured is made up of various liquid compositions if only one flow condition is observed or if the pressure measurements are taken under the wrong range of flow conditions. The present invention provides a method and system for overcoming the deficiencies of conventional prior art vapor pressure measurement systems, particularly of the type utilizing so-called eductor devices.

SUMMARY OF THE INVENTION

The present invention provides an improved method and system for measuring the true vapor pressure of a multi-component liquid utilizing an eductor-type or similar flow device through which the liquid is caused to flow while various pressure measurements are taken, preferably at a constant liquid temperature during the measurement process.

In accordance with one important aspect of the present invention, an improved method of measuring vapor pressure using an eductor is provided wherein the flow rate of the liquid to be measured through the eductor is increased incrementally while the change in the pressure at the suction port is measured as a function of the changing pressure differential across the eductor. The change in slope of a curve generated by the incremental pressure differential changes is observed to indicate the onset of vaporization of the component of the liquid composition having the highest vapor pressure.

In accordance with another aspect of the present invention, a method for measuring the vapor pressure of a multi-component liquid is provided wherein liquid flow through an eductor is measured in terms of the suction port pressure as a function of the pressure differential across the eductor and the second derivative of the relationship between suction port pressure and pressure differential is calculated to determine when the change in slope of the function has a zero value. This point in the change in slope of the suction port pressure-pressure differential function indicates the onset of vaporization of the liquid and thus the true vapor pressure of that liquid. Accordingly, the true vapor pressure of a multi-component liquid may be defined as the highest pressure at which vaporization of any of the components of the liquid begins. For practical purposes in the handling and transport of a multi-component liquid, it is important to know the onset of vaporization of any component of that liquid, particularly for volatile compositions included in crude oils and other hydrocarbon fluids.

In accordance with yet another important aspect of the present invention, an improved vapor pressure measurement system is provided utilizing an eductor device wherein liquid flow through the eductor is incrementally increased while the pressure differential across the eductor as well as the pressure at the eductor suction port is measured. The system is particularly adapted for continuous operation in conjunction with multi-component liquid handling and transport systems.

Those skilled in the art will further appreciate the above-described features and advantages of the present invention as well as other superior aspects thereof upon reading the detailed description which follows in conjunction with the drawing.

DESCRIPTION OF PREFERRED EMBODIMENT

Figure 1:
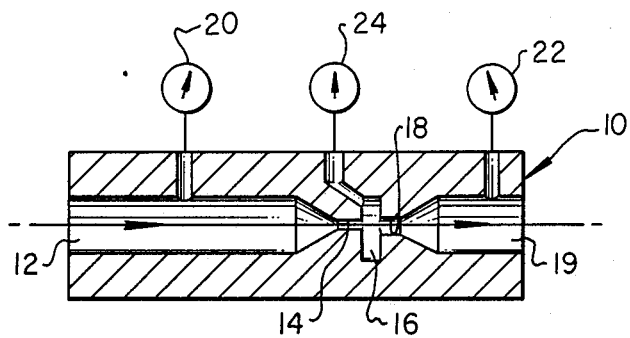
FIG. 1 is a schematic diagram of an eductor of a type which is particularly suitable for use in measuring the vapor pressure of multi-component liquids in accordance with the present invention.

In the description which follows, like parts are marked throughout the specification and drawing with the same reference numerals, respectively. The drawing figures are in schematic or diagrammatic form in the interest of clarity and conciseness.

U.S. Pat. No. 4,733,557 to Lloyd A. Baillie, et al, and assigned to the assignee of the present invention describes a method and system for measuring the vapor pressure of a multi-component liquid such as crude oil utilizing an eductor device. The system and method of the Baillie, et al patent assumes that if a sufficiently large pressure differential is caused to occur across the eductor, by subjecting the liquid to a relatively high flow rate, the pressure condition measured at the so-called suction port of the eductor will be representative of the vapor pressure of the liquid. Although the Baillie patent recognizes that the vapor pressure of a multi-component liquid varies, this patent suggests that selected pressure differentials less than the initial pressure differential across the eductor may be measured and the suction port pressure at these selected pressure differentials recorded to establish the portion of the curve of the suction port pressure-eductor pressure differential function representing the variable vapor pressure condition. The intercept of this portion of the curve with the portion of the curve representing a so-called dead liquid is then selected as the so-called "bubble point" or vapor pressure of the multi-component liquid. However, as will be described herein, for many multi-component liquids, this approach to measuring vapor pressure can introduce a degree of error which may not be acceptable in certain operating conditions or when attempting to accurately measure the true vapor pressure of a particular fluid composition.

Referring to FIG. 1, the system and method of the present invention utilizes a device commonly known as an eductor and generally designated by the numeral 10. The eductor 10 has an inlet passage or port 12 which is reduced in diameter to a smaller diameter or throat portion 14 which opens into a larger diameter chamber 16. The chamber 16 may also be referred to herein as the "suction port" of the eductor 10. Slightly downstream, in the normal direction of flow of fluid through the eductor 10, is a somewhat larger diameter outlet port 18 which has a greater cross-sectional flow area than the throat 14. The port 18 typically opens into a larger passage 19. In the operation of the eductor 10 for performing vapor pressure measurements in accordance with the present invention, the pressure drop across the eductor is measured between pressure measuring devices comprising transducers or gauges 20 and 22.

The so-called suction pressure of the eductor 10 or what is actually the point of measurement of the vapor pressure of the liquid flowing through the eductor is measured at the gauge 24. The pressure at the gauge 20 may be designated as $P_{in}$, the pressure at the gauge 22 may be designated as $P_{out}$ and the pressure at the gauge 24 measuring from the port or chamber 16 may also be designated as $P_{suction}$. When a liquid is caused to flow through the eductor 10, the flow rate of the liquid may be increased such as to transcend from so-called pipe flow conditions to a condition wherein the pressure in the chamber or port 16 is reduced significantly. The eductor may, in fact, be utilized as a vacuum pump or what it sometimes known as an ejector. In any case, the pressure in the chamber or port 16 may be reduced to the point wherein the liquid will vaporize as it passes from the throat 14 to the outlet port 18 and the pressure measured at the gauge 24 will represent the vapor pressure of the liquid composition flowing through the eductor 10. As the flow rate through the eductor 10 is increased from a point at which the pressure differential $P_{in}$ minus $P_{out}$ is nil, the onset of vaporization of the lower molecular weight compositions in the fluid will cause a change in the slope of the curve representing the vapor pressure or $P_{suction}$ pressure as a function of the pressure differential across the eductor ($P_{in}$ minus $P_{out}$).

Figure 2:
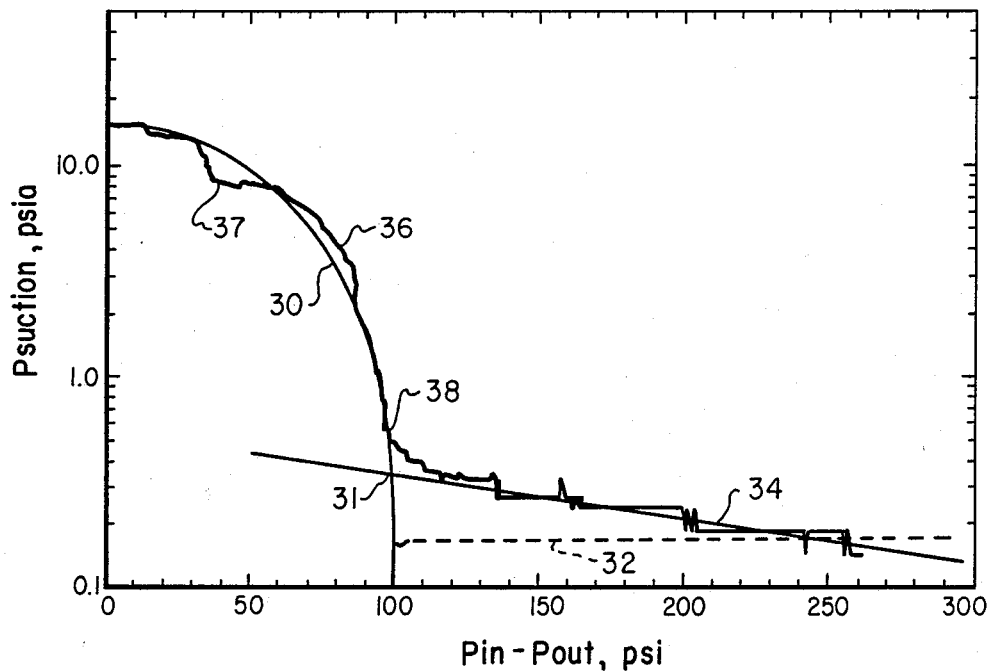
FIG. 2 is a diagram showing the suction port pressure as a function of the pressure differential across an eductor-type measurement device for a multi-component liquid.

Referring now to FIG. 2, there is illustrated a diagram indicating the vapor pressure characteristic of a pure or single composition liquid and the vapor pressure characteristic of a multi-component liquid such as crude oil including lighter or lower molecular weight fluids such as natural gasoline liquids mixed therein, for example. The smooth line curve 30 shows the characteristic of a so-called dead or pure liquid with respect to the measurement of the eductor suction pressure at the gauge 24 as a function of increasing pressure differential measured between the gauges 20 and 22 of the eductor 10. If the liquid did not change state under any pressure condition or was a truly "dead" liquid, the curve 30 would intercept the abscissa at approximately 100 PSI differential pressure, for example. On the other hand, if the liquid was a pure liquid that had a specific vapor pressure at the temperature that the liquid was being caused to flow through the eductor, the suction pressure as a function of increasing differential pressure would reach a certain minimum or the vapor pressure point, as indicated by the line 32. With increasing differential pressure ($P_{in} - P_{out}$), the liquid would continue to vaporize and the pressure at the gauge 24 would remain constant with increasing differential pressure as indicated.

However, a multi-component liquid will not exhibit a constant vapor pressure with increasing pressure differential across the eductor throat since the lower molecular weight liquids will typically begin to vaporize at a higher pressure and, when these liquids have vaporized, the suction port pressure will decrease to the vapor pressure of the heavier molecular weight liquids. Accordingly, the selection of a flow condition through the eductor 10 wherein an arbitrarily large pressure differential is created and then decreased to find changes in vapor pressure as indicated by the line 34 will provide an intercept 31 with the curve 30 but very likely not an accurate measure of the actual onset of vaporization or the "bubble point" pressure of the liquid composition in question. For purposes of this discussion, the so-called bubble point pressure or the initial vapor pressure of a liquid composition will be characterized as the true vapor pressure. Certainly for some liquid handling and transport processes, it is necessary to know the "bubble point" pressure or the highest pressure at which onset of vaporization of at least some component of the liquid composition occurs.

In FIG. 2, the heavy line curve 36 represents the actual vapor pressure characteristic of a multi-component liquid caused to flow through an eductor while increasing the pressure differential across the eductor throat to determine the initial or true vapor pressure of the liquid. As indicated by the curve 36 it generally follows the curve 30 to an inflection point 38 wherein the slope of the curve decreases and with incrementally increasing differential pressure ($P_{in}$ minus $P_{out}$) the slope continues to decrease. This point 38 is indicative of the value of the true vapor pressure of the fluid being measured. One technique for determining the point 38 in accordance with the present invention is to calculate the second derivative of the function of the suction pressure with respect to the pressure differential across the eductor 10. When the second derivative equals zero, this characteristic marks the point of inflection 38 of the curve 36 and yields the value of true vapor pressure of the fluid composition in question.

Determination of the point 38 on the curve 36 may be obtained by conducting vapor pressure measurements with an improved system in accordance with the present invention and which will be described in further detail herein. The method is carried out by increasing the fluid pressure drop across the eductor 10 incrementally while monitoring the pressure drop versus the pressure at the suction port or chamber 16. The incremental change in the suction pressure for each incremental change in pressure drop or differential pressure across the eductor is compared with the previous value of suction pressure as a function of differential pressure across the eductor and when the slope of the curve changes such that the second derivative of the function which represents the curve 36 equals zero, it is indicated that the point 38 has been reached, which corresponds to the true vapor pressure. In order to be sure that the vapor pressure of the fluid being measured has been reached, further incremental increases in the pressure differential ($P_{in}$ minus $P_{out}$) are obtained and the suction pressure at the port 16 measured to be sure that the slope of the curve 36 has continued at the significantly decreased or changed value for a change in the differential pressure across the eductor. In this way, minor variations in the relationship between the eductor suction port pressure and the pressure differential across the eductor are avoided as indicated at 37 in FIG. 2, for example.

One preferred way of determining the inflection point 38 is to use a curve fitting technique known as a cubic spline fit. The mathematical technique known as a cubic spline fit may be carried out on a digital computer using a program basically of the type described in a publication entitled "Numerical Recipes: The Art of Scientific Computing", by W. H. Press et al, Cambridge University Press.

Figure 3:
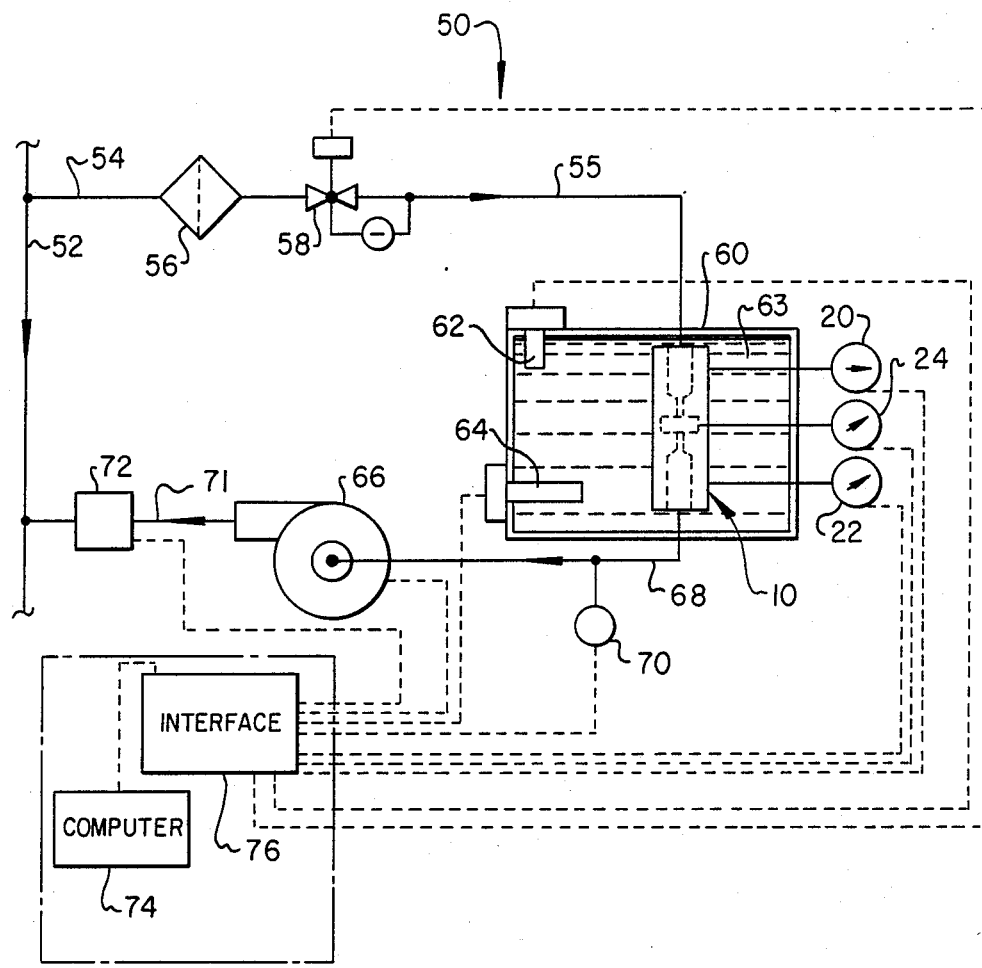
FIG. 3 is a schematic diagram of a vapor pressure measurement system in accordance with the present invention.

Referring now to FIG. 3, there is illustrated in schematic form a diagram of a preferred system for measuring the vapor pressure of a multi-component liquid at a particular temperature condition. The system illustrated in FIG. 3 is generally designated by the numeral 50 and is shown connected to a fluid transmission pipeline 52 for sampling liquid flowing therethrough to determine its vapor pressure from time to time. The system 50 includes a liquid inlet conduit 54 connected to the pipeline 52 for withdrawing liquid therefrom. Preferably, a general purpose liquid filter 56 is interposed in the conduit 54 upstream of a motorized pressure regulating valve generally designated by the numeral 58. The pressure regulating valve 58 is of a general type which is operable to maintain, at a selected valve operating condition, a predetermined pressure in the conduit 55 downstream of the valve in the direction of flow as indicated by the arrows in FIG. 3. Accordingly, for a particular setting of the valve 58, the valve will modulate the flow of liquid through the conduit 54 to maintain the predetermined pressure setting in the conduit on the downstream side of the valve or in the conduit segment indicated by the numeral 55. The conduit segment 55 is connected to the eductor 10 which is disposed in a suitable enclosure 60. The enclosure 60 is preferably fluid tight and adapted to be filled with a heat exchange fluid 63 such as water maintained at a constant temperature so that the temperature of the liquid flowing through the eductor 10 is maintained at a predetermined value while the vapor pressure is being sampled. The enclosure 60 is preferably adapted to be fitted with a liquid level sensor 62 and a heating element 64 which is automatically controlled to maintain the liquid in the enclosure at a predetermined temperature.

The sensor 62 is operable to shut off the heating element 64 in the event of a leak or loss of liquid from the enclosure 60.

The eductor 10 is connected on its downstream side to a pump 66 by way of an eductor outlet conduit 68. A suitable temperature sensor 70 is also interposed in the outlet conduit 68 for monitoring the temperature of the liquid sample. The pump 66 is connected by way of a discharge conduit 71 to the pipeline 52 for returning the liquid sample being analyzed back to the pipeline flow stream. A suitable flow control switch 72 is interposed in the conduit 71 for monitoring flow of liquid through the system and operating the system to shut down if a continuous flow of liquid sample is not being conducted through the conduits 54, 55, 68 and 71.

The operation of the system 50 may be automatically controlled by a digital computer 74 operating through an interface module 76 which is adapted to convert analog data to digital data and vice versa for reading the pressure gauges 20, 22 and 24 and the temperature gauge 70, for controlling the motorized pressure regulator valve 58 and the pump 66 and for controlling the temperature of the heat exchange liquid in the enclosure 60.

In the operation of the system 50, the pump 66 is controlled to operate at a volume flow rate which will assure a significant pressure drop across the eductor 10 when the motorized pressure regulator valve is set to maintain a relatively high pressure in the conduit 55 and the inlet port to the eductor 10. In this way a significant pressure drop across the eductor 10 is assured. The computer 74 and the digital/analog interface module 76 are adapted to be operable, when carrying out a vapor pressure measurement routine, to set the pressure regulator valve 58 initially at a relatively low pressure setting for the pressure in the conduit 55 and sufficiently low to provide essentially zero pressure drop ($P_{out}$ minus $P_{out}$ equals zero) condition across the eductor. This is the starting point of the curve 36 at the ordinate of the diagram of FIG. 2. The regulator valve 58 is then operated to incrementally increase the pressure in the conduit 55 so that incremental changes in the pressure drop across the eductor 10 in increments of, for example, one psi are recorded. For each incremental reading of pressure drop across the eductor, the suction pressure or pressure at the port 16 is read and recorded. These readings are repeated until the pressure drop across the eductor 10 is well into a region which will be known to produce a vapor pressure reading at the pressure transducer or gauge 24. The data set obtained for each operating cycle is then stored in the computer 74 and utilized to perform a curve fitting function using the cubic spline method to develop the curve 36. By taking the second derivative of the function which defines the curve 36 at each reading, the point 38 may be observed when the second derivative is equal to zero. This reading is noted by the system operating program as the true vapor pressure of the sample being analyzed.

Accordingly by measuring the pressure differential across an eductor beginning with a flow condition in the so-called pipe flow regime wherein there is virtually no pressure drop across the eductor throat and incrementally increasing the flow to obtain progressively greater pressure differentials across the eductor while recording the pressure in the suction port of the eductor for each pressure differential condition, the onset of vaporization of the highest vapor pressure component of a multi-component liquid, which is the true vapor pressure of that liquid, is more accurately and easily determined than in accordance with prior art processes. Moreover, the unique system for performing this method is effective yet relatively uncomplicated in that the eductor apparatus itself is inherently mechanically simple and reliable. Moreover, by providing a pressure regulator valve which is capable of being set at selected pressure conditions, a set of data points representing the suction port pressure of the eductor for a given pressure differential across the eductor may be easily obtained.

Those skilled in the art will recognize that vapor pressure measurements may be taken using the method and system of the present invention for a multi-component as well as single component or pure liquid composition. However, the method and system of the present invention is particularly advantageous for making true vapor pressure measurements of various hydrocarbon liquid mixtures including crude oils and certain refined hydrocarbon liquid mixtures.

Although preferred embodiments of the present invention have been described in detail hereinabove, those skilled in the art will recognize that various substitutions and modifications may be made without departing from the scope and spirit of the invention as recited in the appended claims.

What is claimed is:

1. A method for determining the true vapor pressure of a multi-component liquid composition which typically exhibits, at a constant temperature, different vapor pressures due to the vaporization of compositions of different molecular weight in the liquid, comprising the steps of:
   providing an eductor having an inlet port, a suction port, and an outlet port;
   passing a sample of liquid through said eductor at various flow rates while measuring the pressure differential between said inlet port and said outlet port and the pressure at said suction port, said pressure measurements being taken at a flow condition wherein a relatively low pressure differential between said inlet port and said outlet port is exhibited; and
   incrementally changing the flow rate while measuring the pressure differential between said inlet port and said outlet port and recording the suction port pressure at each incremental change in pressure differential at least until a point of inflection is observed in the proportional relationship between the pressure differential and the pressure at the suction port as an indication of the true vapor pressure of the liquid composition.

2. The method set forth in claim 1 including the step of:
   increasing the pressure differential between the inlet port and the outlet port of said eductor substantially beyond the value which provides the point of inflection to confirm that the point of inflection represents the true vapor pressure of the liquid composition.

3. The method set forth in claim 1 wherein:
   the step of incrementally increasing the pressure differential between the inlet port and the outlet port of said eductor is carried out by regulating the pressure of the liquid flowing to said inlet port in incrementally higher steps for each measurement of pressure differential and suction port pressure.

4. A method for determining the true vapor pressure of a liquid composition comprising the steps of:
   providing an eductor apparatus having an inlet port, an outlet port, and a suction port interposed between said inlet port and said outlet port and downstream of a throat portion of said eductor, said eductor including means for measuring the pressure differential between said inlet port and said outlet port, and means for measuring the pressure at said suction port;
   causing said liquid composition to flow through said eductor while causing incremental changes in the pressure differential between said inlet port and said outlet port from a condition where substantially negligible pressure differential between said inlet port and said outlet port is observed to a pressure differential wherein relatively small changes in the suction pressure occur for relatively large changes in the pressure differential occur; and
   determining the pressure at the suction port as a function of the pressure differential between said inlet port and said outlet port and calculating the second derivative of said function to determine where said second derivative equals zero as an indication of the value of suction port pressure corresponding to the true vapor pressure of said liquid composition.

5. The method set forth in claim 4 wherein:
   the step of incrementally increasing the pressure differential between said inlet port and said outlet port is carried out by increasing the liquid pressure at said inlet port.

6. The method set forth in claim 4 wherein:
   the step of incrementally increasing the pressure between said inlet port and said outlet port is carried out at a substantially constant temperature of said liquid.

7. A system for determining the vapor pressure of a liquid composition comprising:
   an eductor including an inlet port, a throat portion, a suction port downstream of said throat portion and a discharge port downstream of said suction port in the direction of flow of liquid through said eductor;
   conduit means connected to said inlet port and conduit means connected to said outlet port for conducting said liquid composition through said eductor;
   pump means interposed in said conduit means connected to said outlet port for causing said liquid composition to flow through said eductor;
   means for measuring the pressure differential between said inlet port and said outlet port and means for measuring the pressure at said suction port while causing liquid to flow through said eductor;
   a pressure regulator valve disposed in said conduit means connected to said inlet port and operable to maintain a predetermined pressure in said conduit means connected to said inlet port between said pressure regulator valve and said inlet port; and
   means associated with said pressure regulator valve for changing the pressure of said liquid composition flowing through said eductor at said inlet port so that a set of incrementally different pressure differentials between said inlet port and said outlet port may be read together with pressures at said suction port for each incremental pressure differential between said inlet port and said outlet port for determining the vapor pressure of said liquid composition.

8. The system set forth in claim 7 including:

enclosure means for enclosing said eductor, said enclosure means providing a liquid filled space which is filled with a liquid at a substantially constant temperature for stabilizing the temperature of said eductor and said liquid composition flowing through said eductor during a process of measuring the vapor pressure of said liquid composition.

* * * * *